(12) United States Patent
Anderson et al.

(10) Patent No.: US 7,563,280 B2
(45) Date of Patent: Jul. 21, 2009

(54) EFFICIENT IMPLANTATION OF HEART VALVE PROSTHESES

(75) Inventors: Kimberly A. Anderson, Eagan, MN (US); Danney J. Langanki, Lino Lakes, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 224 days.

(21) Appl. No.: 10/614,741

(22) Filed: Jul. 7, 2003

(65) Prior Publication Data

US 2004/0078074 A1    Apr. 22, 2004

Related U.S. Application Data

(63) Continuation of application No. 09/561,521, filed on Apr. 28, 2000, now Pat. No. 6,589,279.

(60) Provisional application No. 60/131,351, filed on Apr. 28, 1999.

(51) Int. Cl.
*A61F 2/24* (2006.01)
(52) U.S. Cl. ...................... 623/2.13; 623/2.17; 623/904
(58) Field of Classification Search ......... 623/2.1–2.19, 623/904, 1.26, 910, 922; 606/142, 143, 151, 606/213–221
See application file for complete search history.

(56) References Cited

U.S. PATENT DOCUMENTS

| | | | |
|---|---|---|---|
| 3,587,115 A | 6/1971 | Shiley | |
| 4,470,157 A | 9/1984 | Love | |
| 4,888,009 A | 12/1989 | Lederman et al. | |
| 4,994,073 A | 2/1991 | Green | |
| 5,089,015 A * | 2/1992 | Ross | 606/144 |
| 5,163,955 A | 11/1992 | Love et al. | |
| 5,211,658 A | 5/1993 | Clouse | |
| 5,370,685 A | 12/1994 | Stevens | |
| 5,417,699 A | 5/1995 | Klein et al. | |
| 5,449,384 A * | 9/1995 | Johnson | 623/2.14 |
| 5,531,678 A | 7/1996 | Tomba et al. | |
| 5,827,298 A * | 10/1998 | Hart et al. | 606/139 |
| 5,843,164 A | 12/1998 | Frantzen et al. | |
| 5,843,179 A | 12/1998 | Vanney et al. | |
| 5,855,601 A | 1/1999 | Bessler et al. | |
| 5,954,747 A | 9/1999 | Clark | |
| 6,334,873 B1 | 1/2002 | Lane et al. | |
| 6,402,780 B2 * | 6/2002 | Williamson et al. | 623/2.11 |

FOREIGN PATENT DOCUMENTS

| | | |
|---|---|---|
| DE | 195 32 846 | 3/1997 |
| WO | WO 98/43556 | 10/1998 |

* cited by examiner

*Primary Examiner*—David Isabella
*Assistant Examiner*—Suba Ganesan
(74) *Attorney, Agent, or Firm*—Hallie A. Finucane; Westman, Champlin & Kelly, P.A.

(57) ABSTRACT

Tools can be used to assist with the implantation of heart valve prostheses, especially stentless aortic heart valve prostheses. In some embodiments, a heart valve prosthesis includes a plurality of flexible leaflets, a commissure support and a plurality of fasteners inserted into the inner surface of the commissure support and protruding from the outer surface of the commissure support. The fasteners comprise an elongated portion and a tip at an end of the elongated portion. In other embodiments, a heart valve prosthesis includes a plurality of flexible leaflets and a reinforcement secured to an inner surface of a valve commissure support. The reinforcement has an aperture. The heart valve prosthesis and fastener components can be placed into kits. The fasteners can be used to perform improved implantation procedures.

20 Claims, 4 Drawing Sheets

EFFICIENT IMPLANTATION OF HEART VALVE PROSTHESES

FIELD OF THE INVENTION

This application is a continuation of application Ser. No. 09/561,521, filed Apr. 28, 2000 now U.S. Pat. No. 6,589,279. The application is incorporated herein by reference.

This application claims priority to U.S. Provisional Patent Application Ser. No. 60/131,351 filed Apr. 28, 1999 to Schoon et al., entitled "Tissue Heart Valve Implantation Tool," incorporated herein by reference.

BACKGROUND OF THE INVENTION

The present invention relates to heart valve prostheses. In particular, the present invention relates to aortic heart valve prostheses with an efficient and easy to use fastening system for implantation of the prosthesis.

Prostheses, i.e., prosthetic devices, are used to repair or replace damaged or diseased organs, tissues and other structures in humans and animals. Prostheses must be generally biocompatible since they are typically implanted for extended periods of time. For example, prostheses can include artificial hearts, artificial heart valves, ligament repair material, vessel repair, surgical patches constructed of mammalian tissue and the like.

Prostheses can be constructed from natural materials such as tissue, synthetic materials or a combination thereof. For example, prostheses formed from purely synthetic materials, such as mechanical heart valve prosthesis, can be manufactured from, for example, biocompatible metals, ceramics, carbon materials, such as graphite, polymers, such as, polyester, and combinations thereof. Heart valve prostheses can be formed with rigid occluders or leaflets that pivot to open and close the valve, or with flexible leaflets that flex to open and close the valve.

Although mechanical heart valves with rigid pivoting occluders or leaflets have the advantage of proven durability through decades of use, they are associated with blood clotting on or around the prosthetic valve. Blood clotting can lead to acute or subacute closure of the valve or associated blood vessel. For this reason, patients with implanted mechanical heart valves remain on anticoagulants for as long as the valve remains implanted. Anticoagulants impart a 3-5% annual risk of significant bleeding and cannot be taken safely by certain individuals.

Besides mechanical heart valves, heart valve prostheses can be constructed with flexible tissue leaflets or polymer leaflets. Prosthetic tissue heart valves can be derived from, for example, porcine heart valves or manufactured from other biological material, such as bovine pericardium. Biological materials in prosthetic heart valves generally have profile and surface characteristics that provide laminar, nonturbulent blood flow. Therefore, intravascular clotting is less likely to occur than with mechanical heart valve prostheses.

In the heart, blood flow between the atria and the ventricles and out of the ventricles is controlled by heart valves. Blood flow from the right ventricle of the heart passes into the pulmonary artery. Blood flow from the left ventricle of the heart passes into the aorta. Aortic heart valves are located between the left ventricle and the aorta where the aorta connects with the heart. Similarly, pulmonary valves are located between the right ventricle and the pulmonary artery.

The native aortic heart valve has three leaflets that open to allow flow into the aorta and close to prevent back flow into the left ventricle. Tissue leaflets have sufficient flexibility to open and close. This allows for placement of a prosthetic valve within the aorta at or near the opening into the heart. Each of the three leaflets of a natural valve is attached to the wall of the aorta along a nonplanar curve.

Attachment of the stentless aortic valve prosthesis is complicated since suturing must be performed on both the inflow and outflow edges of the prosthesis to secure the prosthesis. Significant pressures are exerted against the valve in use. Thus, it is desirable to suture the prosthetic valve along the commissure supports to ensure that the valve does not pull away from the aorta or pulmonary artery. That suturing along the commissures is difficult because the valve is within the aorta. Thus, attachment of the valve is further complicated since suturing must be performed on both the inflow and outflow edges of the valve to secure the valve.

SUMMARY OF THE INVENTION

In a first aspect, the invention pertains to heart valve prostheses comprising a plurality of flexible leaflets, a commissure support and a plurality of fasteners inserted into the inner surface of the commissure support and protruding from the outer surface of the commissure support. The fasteners comprise an elongated portion and a tip at an end of the elongated portion.

In a further aspect, the invention pertains to a heart valve prosthesis including a plurality of flexible leaflets and a reinforcement secured to an inner surface of a valve commissure support. In preferred embodiments, the reinforcement has an aperture.

In another aspect, the invention pertains to a kit comprising a heart valve prosthesis, and fasteners. The prosthesis has a plurality of flexible leaflets and commissure supports. The fasteners have an elongated portion and a tip on the end of the elongated portion.

In addition, the invention pertains to a method for attaching a heart valve prosthesis in a patient, the method including inserting a fastener through the prosthesis into an aortic wall or pulmonary artery wall. The prosthesis includes leaflets and valve commissure supports.

Furthermore, the invention pertains to a fastener applicator for implanting a heart valve prosthesis including an inner shaft, an outer shaft, a suture needle, a base plate connecting the inner shaft and the outer shaft, and a handle. The outer shaft has a sleeve and a plurality of pivots such that a section of the outer shaft can fold to extend the sleeve outward relative to the non-folding portion of the outer shaft. The suture needle rests within the sleeve. The handle provides for the relative motion of the inner shaft and the outer shaft through the folding of the outer shaft at the plurality of pivots.

DETAILED DESCRIPTION OF THE PREFERRED EMBODIMENTS

Rigid fasteners can be used, in particular, for attaching an aortic heart valve prosthesis or pulmonary heart valve prosthesis to an aortic wall or root or to a pulmonary artery, respectively. The fasteners have a sharp end such that they can be driven into the aortic wall, and their rigidity prevents collapse of the fastener when driving forces are applied. For simplicity, "aortic wall" is used herein to refer to both the wall of the aorta and the wall of the pulmonary artery. Reinforcements can be used to supplement the fasteners with respect to simplifying the deployment of the fasteners and stabilizing the deployed fasteners. These fasteners and reinforcements create new tools for use in implantation of heart valve prostheses. Using the fasteners and reinforcements described herein, a physician can reduce the time to implant the prosthesis and the complexity of the implantation procedure.

The fastening system described herein is particularly advantageous for the implantation of an aortic heart valve prosthesis with flexible leaflets formed from tissue or polymer. In particular, stentless, tissue prostheses, such as a fixed porcine heart valve, can be effectively implanted with the fasteners. A preferred stentless aortic heart valve prosthesis has a generally circular lower inflow edge and a upper outflow edge outlining the commissure supports and scallops between the commissure supports, although in alternative embodiments, the lower edge can be scalloped also. The commissures are located along the inner surface of the valve on the elevated portions of the commissure supports where adjacent leaflets meet. Both the inflow edge and outflow edge of the valve preferably are secured during implantation of the valve at the junction of the aorta or the pulmonary artery and the ventricle.

Patients that are suitable for valve prosthesis implantation with the fasteners described herein include humans, porcines, bovines, canines and the like. The valve prosthesis is generally positioned such that some portion of the aortic wall overlaps with the valve prosthesis. During implantation, the valve prosthesis is secured to an aortic wall.

The fasteners generally include an elongated portion and a sharp tip. The fasteners can include a blunt head on the end opposite the sharp tip. In use, the fasteners are configured for insertion through the wall of the valve and the aortic wall. Once inserted, the fastener secures the valve to the aortic wall. The fasteners are particularly helpful to secure the commissure supports and scallops of a stentless aortic valve to the aortic wall. Generally, a plurality of fasteners is used to secure each commissure support. The fasteners preferably have a barb near the sharp tip that helps to maintain the fastener in place after insertion through the wall of the aorta.

A fastener can be inserted through a reinforcement element. In preferred embodiments, a reinforcement guides the placement of a plurality of fasteners. Reinforcements are thin strips that can reduce damage to the tissue by the fastener. One or more reinforcements can be placed on the inner wall of the commissure supports along the top edge of an aortic heart valve prosthesis.

A reinforcement member preferably has apertures indicating the placement of fasteners. When deployed, one fastener inserts through an aperture. The reinforcements can be secured to the inner wall of the prosthesis during manufacture using a suitable fastening system. Alternatively, the reinforcements can be secured to the prosthesis during the implantation of the prosthesis into the patient. The reinforcement may be supplied to the physician with the fasteners inserted into the apertures of the reinforcement such that pushing the end of the fastener deploys the sharp tip into the aortic wall. When one or more reinforcements are used, the fasteners may be inserted through the reinforcement, the valve and the aortic wall to secure the components to each other.

The fasteners can be used to implement improved methods of attaching the heart valve prosthesis to the aortic wall. In the improved methods, the fasteners described herein are inserted into the aortic wall after the valve prosthesis has been positioned and the fastener has been inserted through the wall of the valve and, in some embodiments, through a reinforcement. This method advantageously circumvents the need for extensive suturing and/or use of other devices such as staplers, thus, reducing cross-clamp time.

An alternative embodiment of an implantation tool involves the implantation of a plurality of suture needles simultaneously through the prosthetic valve and the wall of the aortic wall. Following insertion of the suture needles, the needles can be used to complete the suturing process. Some embodiments of this fastener applicator provide for the sequential deployment of the needles at different heights within the prosthesis. The implantation tool can be used for mechanical or stented or stentless bioprosthetic valves with pivoting or flexible leaflets. The fastener applicator can be preloaded onto the prosthesis for single suture line valve prostheses, with the suture lines running through a fabric sewing cuff.

A. Heart Valve Prosthesis

The tools described herein can be used to secure a heart valve prosthesis to an aortic wall. Tools as referred to herein include fasteners and/or reinforcements. Preferred heart valve prostheses have flexible leaflets. The heart valve prosthesis used in the present invention can be constructed from natural materials such as tissue, synthetic materials such as polymers or a combination thereof. The valve prosthesis is preferably a tissue valve, in particular, a stentless, porcine tissue valve.

Natural tissue valves can be derived from an animal species, typically mammalian, such as human, bovine, porcine, canine, seal or kangaroo. These tissues can be obtained from, for example, heart valves, aortic roots, aortic walls, aortic leaflets, pericardial tissue such as pericardial patches, bypass grafts, blood vessels, human umbilical tissue and the like. These natural tissues are typically soft tissues, and generally include collagen containing material. The tissue can be living tissue, decellularized tissue or recellularized tissue. Decellularization approaches are described, for example, in U.S. Pat.

No. 5,855,620, incorporated herein by reference, and in published PCT applications WO96/32905 and WO96/03093, both incorporated herein by reference.

Tissue can be fixed by crosslinking. Fixation provides mechanical stabilization, for example by preventing enzymatic degradation of the tissue. Glutaraldehyde or formaldehyde is typically used for fixation, but other fixatives can be used, such as other difunctional aldehydes, epoxides, genipin and derivatives thereof. Tissue can be used in either crosslinked or uncrosslinked form, depending on the type of tissue, use and other factors. Generally, if xenograft tissue is used, the tissue is crosslinked and/or decellularized.

The prostheses can further include synthetic materials, such as polymers and ceramics. Appropriate ceramics include, for example, hydroxyapatite, alumina, graphite and pyrolytic carbon. Appropriate synthetic materials include hydrogels and other synthetic materials that cannot withstand severe dehydration. Heart valve prostheses can include synthetic polymers as well as purified biological polymers. These synthetic polymers can be woven or knitted into a mesh to form a matrix or similar structure. Alternatively, the synthetic polymer materials can be molded or cast into appropriate forms.

Appropriate synthetic polymers include without limitation polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses and similar copolymers. Bioresorbable polymers can also be used such as dextran, hydroxyethyl starch, gelatin, derivatives of gelatin, polyvinylpyrolidone, polyvinyl alcohol, poly[N-(2-hydroxypropyl) methacrylamide], poly (hydroxy acids), poly(epsilon-caprolactone), polylactic acid, polyglycolic acid, poly (dimethyl glycolic acid), poly(hydroxy buterate), and similar copolymers. These synthetic polymeric materials can be woven or knitted into a mesh to form a matrix or substrate. Alternatively, the synthetic polymer materials can be molded or cast into appropriate forms.

Biological polymers can be naturally occurring or produced in vitro by fermentation and the like or by recombinant genetic engineering. Recombinant DNA technology can be used to engineer virtually any polypeptide sequence and then amplify and express the protein in either bacterial or mammalian cells. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

A tissue-based valve prosthesis can maintain structural elements, such as leaflets, from its native form and/or structural elements can be incorporated into the prosthesis from the assembly of distinct pieces of tissue. For example, the valve prosthesis can be assembled from a porcine heart valve, from bovine pericardium or from a combination thereof. Porcine tissue valves, for example, the Toronto SPV® valve marketed by St. Jude Medical, Inc. St. Paul, Minn., can be implanted in the patient using the tools described herein. The Toronto SPV® valve is designed for implantation in an aortic heart valve position. See, for example, David et al., J. Heart Valve Dis. 1:244-248 (1992). It will be appreciated by those skilled in the art that the tools of the present invention are applicable to any valve, especially any tissue valve prosthesis, that is adapted for implanting in a patient.

Figure 1:
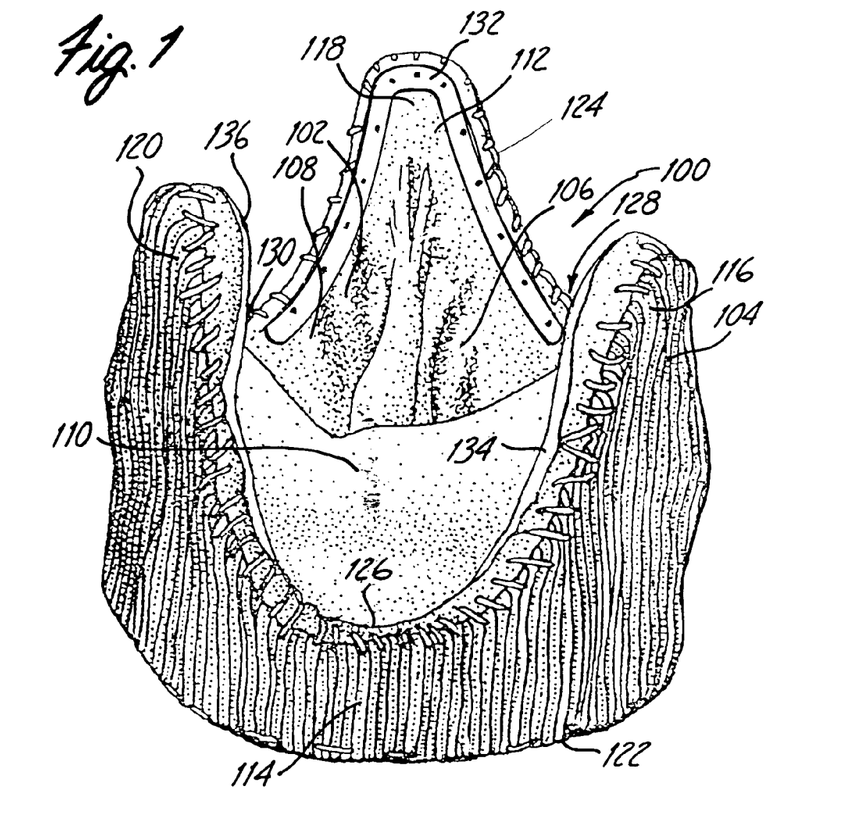
FIG. 1 is a perspective view of an aortic heart valve prosthesis with three flexible leaflets.

An embodiment of a stentless tissue heart valve prosthesis is shown in FIG. 1. Heart valve prosthesis 100 includes a harvested tissue valve 102, such as a crosslinked porcine valve. Prosthesis 100 can further include a sewing cover 104. Valve 102 has three leaflets 106, 108, 110 that meet at commissures 112. A generally cylindrical base 114 and three commissure supports 116, 118, 120 support the leaflets. Lower portion 122 of prosthesis 100 is the inflow edge, and upper portion 124 is the outflow edge. When viewed from the side, commissure supports 116, 118, 120 meet at three scallops 126, 128, 130 along outflow edge 124 of the prosthesis. Lower portion 122 is generally flat, in contrast with the scalloped top portion of the prosthesis. Heart valve prosthesis 100 is shown with optional reinforcements 132, 134, 136.

B. Fasteners

The fasteners can be used to secure an aortic heart valve prosthesis to the aortic wall or an aortic heart valve prosthesis to the pulmonary artery. The fasteners are generally secured to the aortic wall during the implantation procedure of the heart valve prosthesis. The fasteners can have a shape similar to a needle or nail, although the fastener can alternatively have a plurality of sharp tips. In addition, the fasteners preferably have one or more barbs near the tips of the fasteners.

Figure 2:
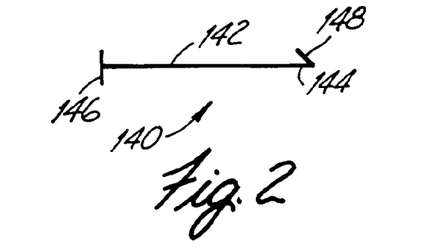
FIG. 2 is a schematic illustration of a fastener.
Figure 3A:
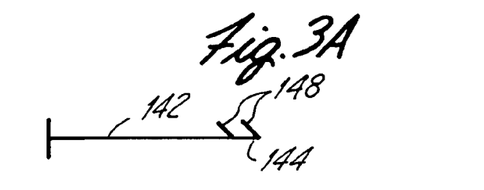
FIG. 3A is a schematic view of a fastener with two barbs.
Figure 3B:
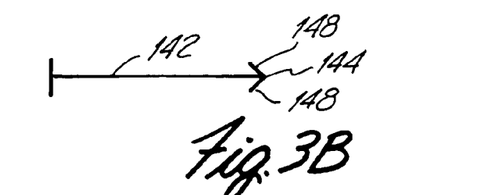
FIG. 3B is a schematic view of an alternative embodiment of a fastener with two barbs.

Referring to FIG. 2, fastener 140 includes an elongated portion 142 with a tip end 144. Fastener 140 has an optional head 146 at the end opposite tip end 144. In preferred embodiments, a barb 148 is located at or near tip end 144. Fastener 140 can include two or more barbs 148 extending from the same or different sides of fastener 140, as shown in FIGS. 3A and 3B.

Figure 4A:
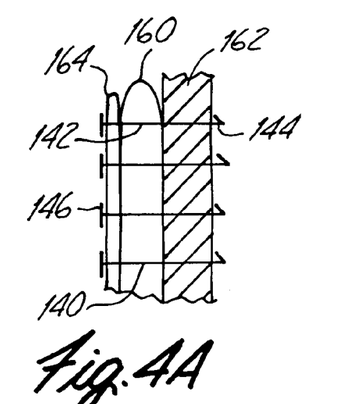
FIG. 4A is a sectional side view of a commisssure support secured to the aortic wall with a reinforcement and fasteners.
Figure 4B:
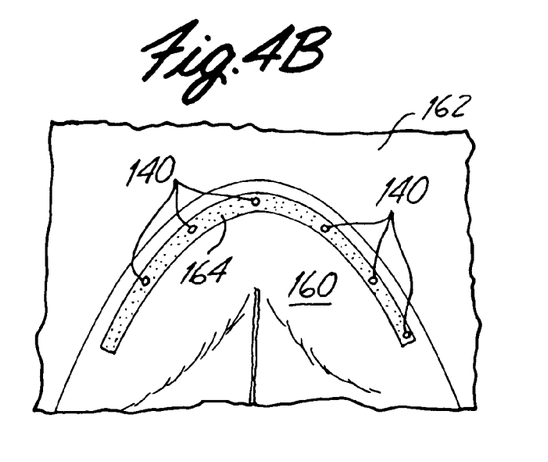
FIG. 4B is a front view of one of the valve commissure supports having a reinforcement secured along the edge of the commissure support.

Referring to FIG. 4A, tip end 144 of fastener 140 can be inserted through a commissure support 160 of the valve prosthesis and through the aortic wall 162. An optional reinforcement 164 can be used, as described further below. Elongated portion 142 of fastener 140 traverses through the reinforcement, if used, the prosthesis and the aortic wall. The fastener, thus, secures the reinforcement and the prosthesis to the aortic wall. Generally, a plurality of fasteners is used to secure a commissure support to the aortic wall, as shown in FIGS. 4A and 4B.

Figure 5:
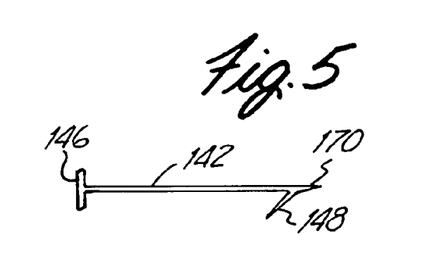
FIG. 5 is a side view of a fastener with a tapered tip and a single barb.

Tip end 144 is generally shaped for insertion into the prosthesis and through the aortic wall. For example, a tip end 170 of the fastener can be tapered, as shown in FIG. 5. A tapered tip provides easier insertion when pressure is applied to the fastener by a physician using finger pressure or an appropriate tool. The fastener also preferably produces little or no damage to the prosthesis or to the aortic wall during insertion.

Referring to FIG. 2, fastener 140 may also include a head 146. Head 146 can facilitate driving fastener 140 through the prosthesis and the aortic wall and can stabilize the fastener following insertion by inhibiting the separation of the prosthesis from the aortic wall or pulmonary wall. Head 146 of fastener 140 generally does not travel through any of the layers, as shown in FIG. 4A. Head 146 is generally larger than the diameter of elongated portion 142. Head 146, for example, can be a flat plate like structure, as shown in FIG. 2. Alternatively, head 146 can be curved if there is a suitable tool for driving the fastener with a curved head. In other alternative embodiments, fastener 140 does not include a head that has a larger diameter than elongated portion 142. In these embodiments, elongated portion 142 simply ends at a flat or curved surface.

Figure 6:
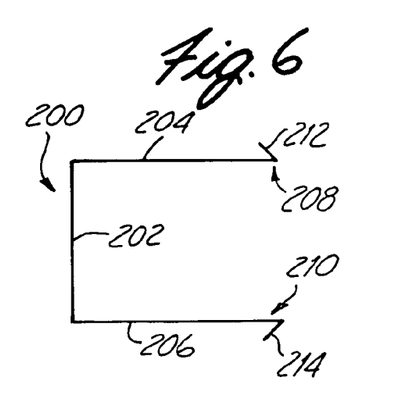
FIG. 6 is a schematic view of a fastener with two tips.

An alternative embodiment of a fastener is shown in FIG. 6. Fastener 200 has a crossbar 202 and two elongated portions 204, 206 connected to crossbar 202. Elongated portions 204, 206 have tips 208, 210 each with barbs 212, 214. When deployed, both tips 208, 210 of fastener 200 are inserted through a reinforcement, if used, the prosthesis and the aortic wall. Fasteners 200 may be simply inserted by a physician exerting finger pressure on crossbar 202 of fastener 200 or using an appropriate tool, such as forceps or a pusher tool. In use, both tips 208, 210 preferably are secured through the outer surface of the aortic wall. Similarly, other fastener embodiments can include more than two tips.

The fasteners are formed from a biocompatible material. Preferable biocompatible materials for the fasteners yield the desired mechanical properties with respect to, for example, durability, mechanical strength, and flexibility/rigidity. Fasteners are sufficiently rigid to hold their shape when pressure is applied by a physician to insert the fastener. A fastener that is not sufficiently rigid may bend when pressure is applied for insertion. Some bending may be tolerable as long as the fastener is able to penetrate the materials. A fastener without sufficient rigidity may not insert properly, thus increasing the propensity of prosthesis damage, aortic wall damage, improper attachment of the prosthesis and/or increased cross-clamp times.

After implantation, the fasteners generally remain in the patient to secure the valve prosthesis for the life-span of the prosthesis or at least until the healing process secures the valve to the aorta through cellular growth, if a bioresorbable material is used for the fastener. The fasteners can be made from, for example, metal, ceramic, polymers or combinations thereof. Suitable metals include, for example, titanium and stainless steel. Suitable ceramics include, for example, hydroxyapatite, such as bone fragments, carbon materials, such as graphite, and alumina. Suitable polymers include sufficiently rigid polymers, such as polyetheretherketone (PEEK). The fasteners can also be formed from bioresorbable polymers, as described above, such that over time the fasteners are resorbed after sufficient tissue has been generated to secure the valve prosthesis without the fasteners.

In preferred embodiments, the fastener is long enough to extend through any reinforcement, the thickness of the prosthesis and the thickness of the aortic wall. Thus, the preferred length depends on the thickness of each of these structures. The length of the fastener elongated portions from the tip to the respective head, blunt end or crossbar is generally less than about one centimeter. The length of the fastener preferably is between about 2 millimeters (mm) and about 8 mm and more preferably about 4 mm to about 7 mm. The diameter of the elongated portion is generally less than about 2 mm, preferably between about 0.2 mm and about 1.5 mm, more preferably between about 0.2 mm and about 1 mm.

C. Reinforcement

A reinforcement may be placed along the inner surface of the valve commissure supports and/or scallops. In alternative embodiments, the reinforcement is placed on the outer surface of the valve, such as at the valve commissure supports. The reinforcement preferably includes apertures through which the fasteners extend or can be inserted. The reinforcements are thin strips of relatively strong material. The reinforcement can prevent or reduce damage to the prosthesis when the fasteners are inserted and after implantation of the heart valve prosthesis in the patient. The reinforcement, thus, can protect and support the commissure supports from potential damage generated by the presence of the fasteners. In alternative embodiments, the reinforcement is placed on the outside of the aorta such that the fastener pierces the reinforcement after passing through the prosthetic valve.

When one or more reinforcements are used, the tip end of the fastener is inserted through the reinforcement, through the prosthesis and through the aortic wall before being secured to the outer surface of the aortic wall, as shown in FIGS. 4A and 4B. The head of the fastener is generally retained on or near the inner surface of the reinforcement. A plurality of embodiments of reinforcements are shown in FIGS. 7A-7D. The selection of the size and shape of the one or more reinforcements are described further below. Reinforcements 250, 252, 254, 256 include one or more apertures 258.

An aperture in the surface of the reinforcement may not go all the way through the reinforcement until the fastener is deployed, although in preferred embodiments, the apertures go through the entire thickness of the reinforcement. The diameter of the apertures generally is approximately the diameter of the elongated portion of a fastener, such that the fastener can be inserted through the aperture, accounting for any barbs. Also, the aperture retains the fastener after deployment of the fastener so that the fastener does not change position. Apertures that are too large can cause the head or end of the fastener to go through the aperture, such that the fastener does not hold the reinforcement against the valve.

The reinforcement can be supplied for use with fasteners inserted into the reinforcement apertures. The selected number and size of the reinforcement may depend on the method of securing the reinforcement and the materials used for the reinforcement. For example, if the reinforcements are stiff, the number, shape and size of the reinforcements can be selected to yield the desired flexibility of the resulting implanted prosthesis. Also, if the reinforcements are applied to the wall of the prosthesis by the surgeon during implantation, fewer numbers of larger reinforcements may simplify the procedure. The reinforcements may be sized such that one reinforcement is sufficient for each prosthesis. In more preferred embodiments, each commissure support is associated with one reinforcement and each lower portion of the scallops formed between the commissure supports includes one reinforcement. In these embodiments, six reinforcements would be used with a three leaflet valve.

Figure 7A:
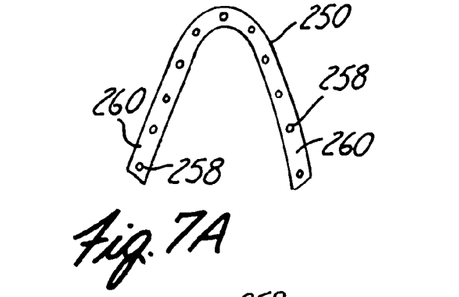
FIG. 7A is a side view of a reinforcement for use on a commissure support.
Figure 7B:
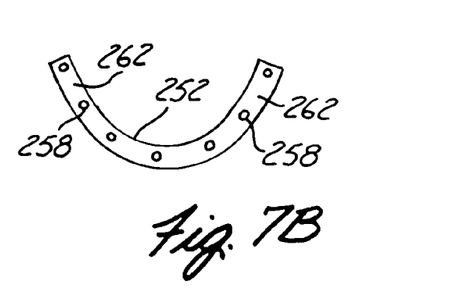
FIG. 7B is a side view of a reinforcement for use on the bottom curve of scallops formed between the commissure supports.
Figure 7C:
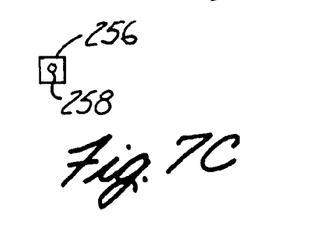
FIG. 7C is a side view of a reinforcement for use with two fasteners.
Figure 7D:
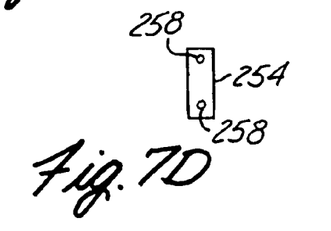
FIG. 7D is a side view of a reinforcement for use with a single fastener.

A reinforcement suitable for one commissure support (such as 116, 118, 120 of FIG. 1) is shown in FIG. 7A as reinforcement 250, and a reinforcement suitable for a lower portion of the scalloped edge (such as 126, 128, 130 of FIG. 1) of the prosthesis is shown in FIG. 7B as reinforcement 252. Legs 260, 262 of, respectively, reinforcements 250, 252 could alternatively be shortened (lengthened) so that reinforcements 250, 252 have a smaller (larger) "u" or inverted "u" shape. If desired, each fastener can be associated with a single small reinforcement 256 (FIG. 7D) or, for example, two fasteners can be associated with each reinforcement 254 (FIG. 7C). Thus, a variety of different numbers of reinforcements can be used for insertion of a particular number of fasteners.

The appropriate length of a reinforcement depends on the number of reinforcements used for implantation and the particular location for use of a reinforcement. The width is generally somewhat wider than the diameter of the apertures, although the width does not have to be constant along the length. For example, the width can narrow between apertures. Generally, the width is selected to be wide enough to provide desired amounts of mechanical strength. Generally, the reinforcement is thin enough not to interfere with the function of the valve while providing the desired mechanical strength. A reinforcement generally is less than about 2 mm thick, preferably no more than about 1 mm thick and more preferably from about 0.2 mm to about 0.5 mm thick.

The reinforcements can be derived from a variety of biocompatible materials. Preferably, the reinforcement has sufficient flexibility such that the native compliance of the leaflets, valve commissures and the aortic wall are not significantly reduced. The reinforcements can be formed from, for example, metal, ceramics, polymers, tissue and combinations thereof. Suitable biocompatible metals, ceramics and polymers are described above. Suitable tissue includes, for example, fascialate or pericardial tissue, such as crosslinked bovine pericardial tissue. Preferred materials include polymers, including relatively rigid polymers, such as polyetheretherketone and polytetrafluoroethylene, flexible polymers, such as silicone polymers (polysiloxanes) and Dacron® polyesters, tissue, and resorbable polymers, such as those described above. Polymers can be woven into fabrics or molded into a solid material. Bioresorbable polymers degrade post implantation, preferably at a rate that allows good tissue incorporation, approximately 4-6 months.

D. Attachment of the Prosthesis

Improved methods of attaching a heart valve prosthesis to a aortic wall can be based on the fasteners and the reinforcements described herein. The reinforcements, themselves, need to be secured either with the fastener or other device. The fasteners can be deployed to secure all of the elements simultaneously or one or more components can be associated with each other or the valve prosthesis prior to the final deployment of the fasteners.

As with any open heart procedure, the process is initiated by placing the patient on appropriate life support and by opening the chest cavity to make the heart accessible. Then, a transverse aortotomy is performed to make the natural valve accessible through the aorta. The preferred location for opening the aorta may depend on precise structure of the prosthesis. For a St. Jude Medical Toronto SPV® prosthesis, the aorta generally is cut about 1 cm from the sinotubular junction. The damaged or diseased natural valve is removed, preferably along with all calcium and calcific debris.

The aortic valve prosthesis generally is placed between the aortic annulus, a slight narrowing where the aorta joins the heart, and the sinotubular junction, a slight narrowing of the aorta just down stream from the coronary arteries. However, the prosthesis can extend beyond the aortic annulus and/or the sinotubular junction. For placement at the aortic annulus, the prosthesis can be parachuted down the severed aorta.

Generally, the heart valve prosthesis is positioned at the site of implantation, adjacent to the appropriate vasculature, typically an aorta. In preferred embodiments, the inflow edge of the valve is sutured or otherwise secured prior to securing the outflow edge with the fasteners described herein, although the inflow edge can be secured after the outflow edge. In addition, it may be desirable to tack the commissures in place prior to application of the fasteners described herein.

In a first approach, the fasteners, the reinforcements, if any, and the prosthesis are all separate at the start of the implantation procedure. With the prosthesis properly aligned, a reinforcement is placed in position and fasteners are sequentially inserted into an aperture in the reinforcement, through the prosthesis and through the aortic wall. When all the fasteners have been inserted through one reinforcement, any additional reinforcements are similarly secured with fasteners. The fasteners can be inserted using finger pressure, forceps, a pusher tool, a hammer, or the like. Specific forceps can be used that specifically interface with the head of a fastener. If there are no reinforcements, the fasteners are placed in a desired position and similarly inserted through the prosthesis and aortic wall.

In some preferred embodiments, fasteners are inserted into reinforcements prior to the initiation of the implantation procedure. The reinforcements can be supplied to the surgeon with the fasteners inserted through or partly through apertures in the reinforcement. In these embodiments, the head or blunt end of the fasteners stick out from the surface of the reinforcements. Thus, the procedure may be somewhat simplified relative to a procedure in which all of the components are separate prior to beginning the procedure. In these embodiments, once the prosthesis is correctly positioned in the aorta, a reinforcement with fasteners is aligned at a desired location, and the fasteners are directly deployed by pushing the fastener through the prosthesis and through the wall of the aorta. The fasteners are inserted sequentially, and a plurality of reinforcements can be secured in this approach.

In alternative embodiments, one or more reinforcements are attached to the prosthesis prior to beginning the implantation procedure. The reinforcements can be secured to the prosthesis by the manufacturer. Suture, biocompatible adhesive or other suitable fastener can be used to secure a reinforcement to the prosthesis. Suitable biocompatible adhesives include, for example, fibrin glue and other surgical glues. Once the prosthesis is correctly positioned, fasteners are sequentially or simultaneously placed within an aperture in the reinforcement and inserted through the prosthesis and the wall of the aorta. This is continued until all of the fasteners are deployed.

In still other embodiments, the prostheses are supplied with reinforcements in place and fasteners inserted in the reinforcements. The reinforcements can be secured to the prosthesis using the fastener inserted through the reinforcement and, at least, partly through the prosthesis. Alternatively, the reinforcement can be secured to the prosthesis using suture, adhesive or other fastener. Once the prosthesis is in place within the patient, each fastener is pushed through the wall of the aorta to secure the prosthesis.

The use of fasteners for securing the valve prosthesis to the aortic wall is advantageously efficient. The use of conventional sutures, while effective and straightforward, can be time-consuming and challenging to maneuver in the appropriate openings for applying the sutures. A particular advantage of the present invention is that once the valve prosthesis is in position, the physician can secure the prosthesis quickly and easily without complicated maneuvers. If rigid reinforcements are used, the reinforcements help to shape the commissure supports, making it easier to place the valve and to ensure maximum valve performance.

E. Distribution and Packaging

The prostheses, fasteners and reinforcements can be distributed in a variety of combinations. Generally, each of the separately packaged components are packaged in sealed, sterile containers. Tissue containing prostheses generally are stored in a moist environment, and can be stored immersed in aqueous glutaraldehyde or other sterile aqueous liquid. The containers can be dated such that the date reflects the maximum advisable storage time. The containers generally are packaged with instructions for the use of the medical devices along with desired and/or required labels. The containers are distributed to health care professionals for surgical implantation of the prostheses.

The various components can be distributed as kits. For example, kits can be distributed with fasteners and reinforcements. The kits can include, in some embodiments, heart valve prosthesis, fasteners and, optionally reinforcements. All of these components can be loose, i.e. unattached in the kit. Alternatively, the components can be partially assembled. For example, the fasteners can be inserted into apertures in the reinforcements, or the reinforcements can be attached to the valve, or all three components can be associated with each other in the kit. The implantation would proceed appropriately, according to the description above.

It will be understood that the specific methods used for implanting the valve prosthesis will vary depending on the components that are included, i.e. extent of attachment of the components. The kits can include instructions to the physician regarding protocols for implantation of the valve prosthesis. The specific protocols may vary based on the specific nature and contents of the kits.

F. Alternative Embodiment Employing A Plurality of Suture Needles

An alternative embodiment of a fastening system for a heart valve prosthesis is shown in sectional view in FIGS. 8A-E at different stages of deployment. Fastener applicator 300 includes an outer shaft 302, an inner shaft 304, an optional spring 306 biasing inner shaft 304 and outer shaft 302, pivots or hinges 308 connected to outer shaft 302 and suture needles 310. Suture (not shown) extends from each suture needle 310. Spring 306 preferably applies force to extend outer shaft 302 relative to inner shaft 304 such that pivots 308 are in an extended configuration, as shown in FIG. 8A. Spring 306 can be replaced with a knob that provides for the relative motion of inner shaft 304 and outer shaft 302.

Inner shaft 304 connects with base plate 313 that links outer shaft 302 and inner shaft 304. In the sectional view of FIG. 8A, two suture needles are shown. In preferred embodiments, additional suture needles are distributed around the circumference of outer shaft 302, preferably at least 8 needles, more preferably at least 10 needles and even more preferably at least 12 needles. Needles 310 rest within sleeves 312. Needles can be placed at different heights along outer shaft 302 such that the needles are not deployed in the same plane. The needles can be positioned to deploy, for example, along commissure supports.

Figure 8:
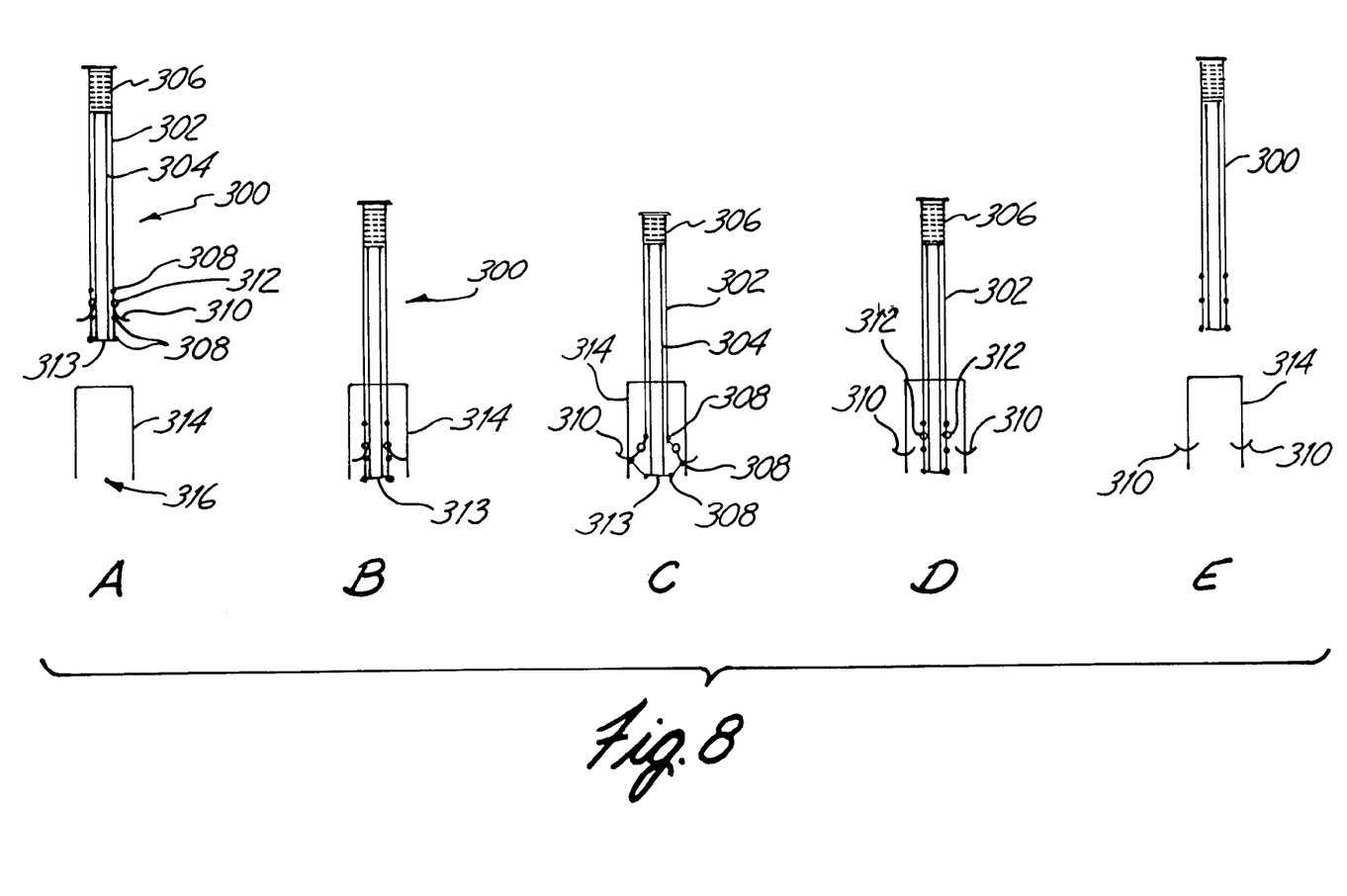
FIGS. 8A-E are sectional views of a fastener applicator for the deployment of suture needles, with each figure corresponding to a different stage of deployment of the needles, the cross section being taken through the center of the fastener applicator, with hidden structure being shown for clarity.

For deployment, fastener applicator 300 is lowered into position from above prosthesis 314, shown schematically in FIG. 8. Inflow edge 316 of prosthesis 314 is shown at the bottom of the prosthesis.

As shown in FIG. 8B, fastener applicator 300 is lowered into position within prosthesis 314 when prosthesis 314 is correctly positioned within the aortic wall. As depicted in FIG. 8C, spring 306 is compressed to lower outer shaft 302 relative to inner shaft 304, thereby bending outer shaft 302 at pivots 308. Needles 310 then pierce prosthesis 314 and the wall of the aorta surrounding prosthesis 314. Needles 310 can be barbed to secure the needles through the wall of prosthesis 314. Referring to FIG. 8D, upon releasing spring 306, outer shaft 302 resumes its extended configuration, and needles 310 release from sleeves 312 due to forces holding needles 310 through the wall of prosthesis 314. Fastener applicator 300 can then be removed from valve prosthesis 314, leaving behind suture needles 310, as shown in FIG. 8E. With single suture valves, the valve can be preloaded onto the fastener applicator with the suture lines running through a fabric sewing cuff.

In the embodiment shown in FIGS. 8A-E, all of the suture needles are deployed simultaneously in a single plane or in different planes. An alternative embodiment is shown in FIGS. 9A-E. Fastener applicator 350 includes a fixed inner shaft 352 attached to a base plate 354 and a folding, segmented outer shaft 356 also connected to base plate 354. Inner shaft 352 and segmented outer shaft 356 connect with a correspondingly segmented knob 358. Segmented outer shaft 356 includes a plurality of segments 360 that can move relative to each other. Generally, a suture needle 362 is attached to each segment 360. Fastener applicator 350 is depicted with 12 suture needles 362 around the circumference of outer shaft 356, although a different number of suture needles can be used if desired. As with the embodiment in FIG. 8, the needles can be placed at the same height or at different heights along outer shaft 356.

Figure 9:
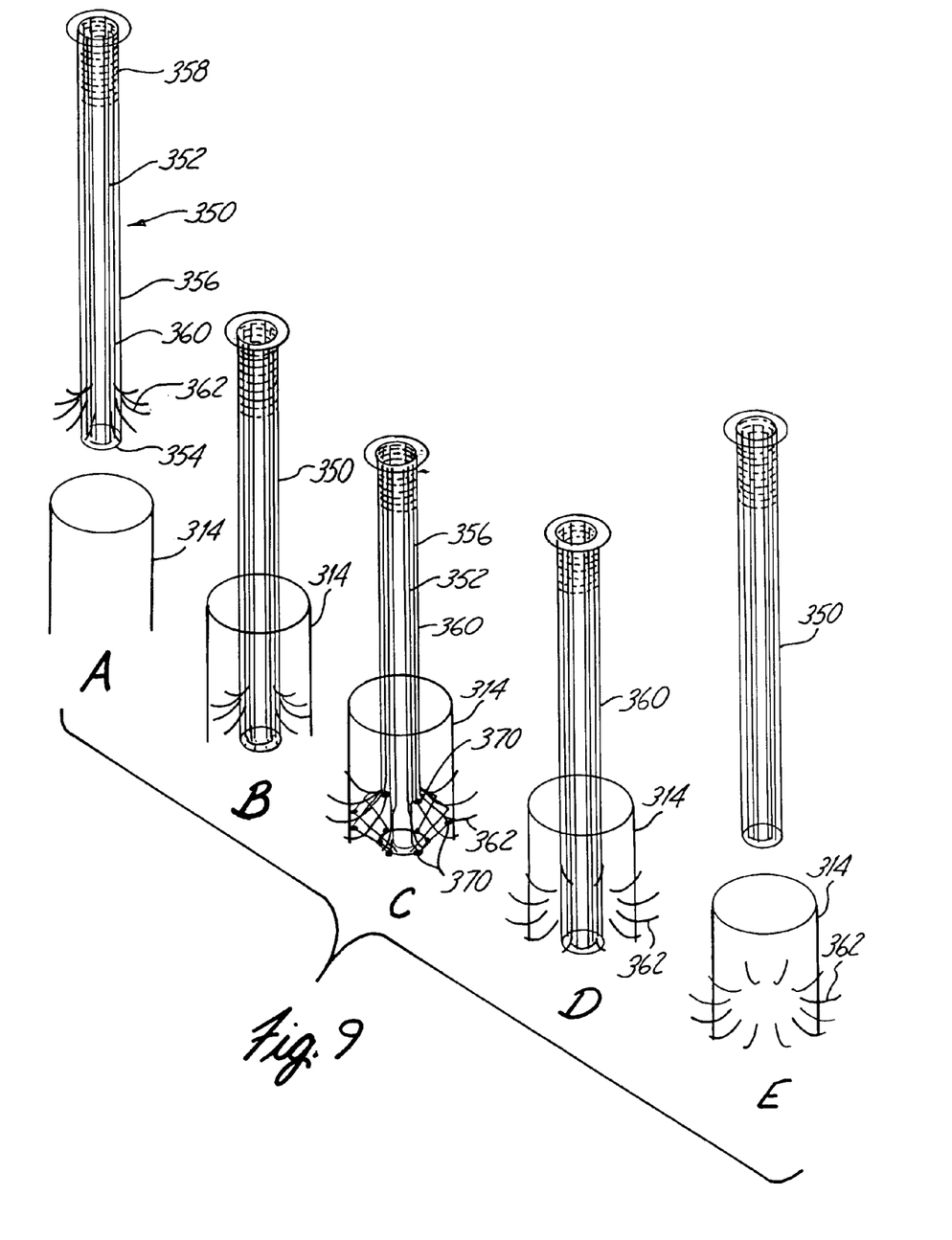
FIGS. 9A-E are perspective views of an alternative embodiment of a fastener applicator for the deployment of a plurality of suture needles with each figure corresponding to a different stage of deployment of the needles, hidden structure being shown for clarity.

Fastener applicator 350 can be positioned within valve prosthesis 314, as shown in FIG. 9B. Moving a segment 360 of outer shaft 356 downward relative to inner shaft 352 results in bending of pivots 370 and the piercing of prosthesis 314 by the corresponding needle 362, as shown in FIG. 9C. In FIG. 9C, all of the segments are simultaneously moved. However, if desired, each segment can be moved individually such that the needles can be deployed sequentially. By moving the position of the fastener applicator between the deployment of different needles, the needles are deployed at different heights along prosthesis 314. Deployment at different heights is particularly advantageous for the placement of suture needles along commissure supports of prosthesis 314. Thus, the needles can be deployed in different planes by sequentially deploying the needles and/or by constructing the device with the needles at different heights. When a segment 360 of outer shaft 356 is returned to its extended position, needles 362 are released, as shown in FIG. 9D. When all of the needles are released, the fastener applicator 350 can be removed from the prosthesis 314, leaving behind needles 362, as shown in FIG. 9E. Again, for the implantation of single suture line mechanical or stented tissue valves, the valve can be preloaded onto the fastener applicator with suture lines running through a fabric sewing cuff.

After the deployment of all of the suture needles using the appropriate embodiment of the fastener applicator, the surgeon can pull the needles through the prosthesis and back through following conventional suturing techniques. The suture can be tied off to complete the suturing process. The deployment of the suture needles with the fastener applicator can facilitate and speed the suturing process. The fastener applicators described above preferably are distributed in a sterile container ready for use.

The embodiments described above are intended to be illustrative and not limiting. Additional embodiments are within the claims below. Although the present invention has been described with reference to preferred embodiments, workers skilled in the art will recognize that changes may be made in form and detail without departing from the spirit and scope of the invention.

What is claimed is:

1. A method for attaching a heart valve prosthesis in a patient, the method comprising:

providing a fastener having a head and a sharp tip, a prosthesis, and a separate reinforcement, the reinforcement comprising a first leg and a second leg connected together with a top portion;

positioning the prosthesis comprising leaflets with a plurality of commissure supports separated by a plurality of scallops in a selected position proximate an aortic wall, a root, or a pulmonary artery wall;

positioning the reinforcement along an inner surface of at least one of the commissure supports, wherein the reinforcement has at least one aperture, wherein an end of the first leg extends to a first scallop and an end of the second leg extends to a second scallop, wherein the reinforcement is configured to be positioned proximate a curved outflow edge of the at least one commissure supports; and inserting the tip of the fastener through the at least one aperture in the reinforcement, the prosthesis and the aortic wall or root or the pulmonary artery wall to attach the heart valve prosthesis in a patient.

2. The method of claim 1 wherein the heart valve prosthesis comprises a stentless porcine valve.

3. The method of claim 1 wherein each of the commissure supports of the prosthesis comprises at least one reinforcement.

4. The method of claim 1 wherein a plurality of fasteners are inserted to secure the prosthesis to the aortic wall or root or the pulmonary artery wall.

5. The method of claim 4 wherein the fasteners are inserted along a curvilinear path.

6. The method of claim 1 wherein the fastener further comprises an elongated portion, the tip at an end of the extended portion and the head on the end opposite the tip, the tip passing through the commissure support and through the aortic wall or root or the pulmonary artery wall to secure the prosthesis to the aortic wall or root or the pulmonary artery wall.

7. The method of claim 6 further comprising providing the head of the fastener with a shape such that the head is larger than a diameter of the elongated portion of the fastener.

8. The method of claim 6 wherein the elongated portion of the fastener extends through the prosthesis and the aortic wall or root or the pulmonary artery wall to secure the prosthesis to the aortic wall or root or the pulmonary artery wall.

9. The method of claim 1 further comprising providing a barb on the tip of the fastener to maintain the fastener in place after insertion.

10. The method of claim 1 wherein the heart valve prosthesis comprises a tissue valve.

11. The method of claim 1 wherein the heart valve prosthesis comprises a polymer valve.

12. The method of claim 1 wherein the prosthesis further comprises a second reinforcement attached to a scallop formed between the commissure supports of the prosthesis, the reinforcement having apertures for insertion of the fastener.

13. The method of claim 1 wherein the tip of the fastener is tapered.

14. A method for attaching a heart valve prosthesis in a patient, the method comprising:
providing a separate reinforcement having at least one aperture, the reinforcement comprising a first leg and a second leg connected together with a top portion;
providing a fastener having a head and a sharp tip;
inserting the fastener through the at least one aperture in the reinforcement;
positioning a prosthesis comprising leaflets with a plurality of commissure supports separated by a plurality of scallops in a selected position proximate an aortic wall, a root, or a pulmonary artery wall;
positioning the reinforcement along an inner surface of at least one of the commissure supports, wherein an end of the first leg extends to a first scallop and an end of the second leg extends to a second scallop, wherein the reinforcement is configured to be secured proximate a curved outflow edge of the commissure supports; and
inserting the tip of the fastener through the prosthesis and through an aortic wall or root or a pulmonary artery wall to attach the heart valve prosthesis to a patient.

15. The method of claim 14 wherein each of the commissure supports of the prosthesis comprises at least one reinforcement.

16. The method of claim 14 wherein a plurality of fasteners are inserted to secure the prosthesis to the aortic wall or root or the pulmonary artery wall.

17. The method of claim 14 wherein the fastener further comprises an elongated portion, the tip at an end of the extended portion and the head on the end opposite the tip, the tip passing through the commissure support and through the aortic wall or root or the pulmonary artery wall to secure the prosthesis to the aortic wall or root or the pulmonary artery wall.

18. A method for attaching a heart valve prosthesis in a patient, the method comprising:
providing a fastener having a head and a sharp tip, a prosthesis, and a separate reinforcement, the reinforcement comprising a first leg and a second leg connected together with a top portion;
positioning the prosthesis comprising leaflets with valve commissure supports separated by a plurality of scallops in a selected position proximate an aortic wall, a root, or a pulmonary artery wall;
positioning the reinforcement along an outer surface of the prosthesis, the reinforcement having at least one aperture, wherein an end of the first leg extends to a first scallop and an end of the second leg extends to a second scallop, wherein the reinforcement is configured to be proximate a curved outflow edge of the prosthesis;
inserting the tip of the fastener through the prosthesis, the at least one aperture in the reinforcement, and through an aortic wall or root or a pulmonary artery wall to attach the heart valve prosthesis to the patient.

19. The method of claim 18 wherein the reinforcement is positioned along at least one of the valve commissure supports along the outer surface of the prosthesis.

20. The method of claim 18 wherein the reinforcement is positioned on the outside surface of the aorta.

* * * * *